United States Patent [19]

Doessel et al.

[11] Patent Number: 4,946,759

[45] Date of Patent: Aug. 7, 1990

[54] POSITIVE RADIATION-SENSITIVE MIXTURE AND RADIATION-SENSITIVE RECORDING MATERIAL PRODUCED THEREFROM

[75] Inventors: Karl-Friedrich Doessel, Wiesbaden; Ralph Dammel, Mainz-Bretzenheim; Juergen Lingnau, Mainz-Laubenheim, all of Fed. Rep. of Germany

[73] Assignee: Hoechst Aktiengesellschaft, Frankfurt am Main, Fed. Rep. of Germany

[21] Appl. No.: 243,792

[22] Filed: Sep. 13, 1988

[30] Foreign Application Priority Data

Sep. 13, 1987 [DE] Fed. Rep. of Germany ....... 3730787

[51] Int. Cl.$^5$ .......................... G03C 1/52; G03C 5/00
[52] U.S. Cl. ..................................... 430/270; 430/311; 430/326; 430/197; 430/177; 522/105
[58] Field of Search ............... 430/326, 177, 270, 179, 430/311; 522/105

[56] References Cited

U.S. PATENT DOCUMENTS

| | | | |
|---|---|---|---|
| 3,779,778 | 12/1973 | Smith | 96/115 |
| 3,887,710 | 6/1975 | Shaver et al. | 424/300 |
| 3,917,483 | 11/1975 | Limburg et al. | 430/326 |
| 4,101,323 | 7/1978 | Buhr et al. | 96/35 |
| 4,247,611 | 1/1981 | Sander et al. | 430/286 |
| 4,248,957 | 3/1981 | Sander et al. | 430/270 |
| 4,250,247 | 2/1981 | Sander et al. | 430/270 |
| 4,311,782 | 1/1982 | Buhr et al. | 430/270 |
| 4,421,844 | 12/1983 | Buhr et al. | 430/326 |
| 4,460,445 | 7/1984 | Rekers | 204/159.2 |
| 4,478,977 | 10/1984 | Sperry et al. | 525/61 |
| 4,617,250 | 10/1986 | Nakakita et al. | 430/175 |
| 4,659,643 | 4/1987 | Ishida et al. | 430/157 |
| 4,659,645 | 4/1987 | Frommeld et al. | 430/175 |
| 4,642,282 | 2/1987 | Stahlhofen | 430/165 |
| 4,737,426 | 4/1988 | Roth | 430/17 |

FOREIGN PATENT DOCUMENTS 3544165 6/1986 Fed. Rep. of Germany .
3601264 7/1986 Fed. Rep. of Germany .

OTHER PUBLICATIONS

Grant and Hackh's Chemical Dictionary, fifth edition, McGraw-Hill Book Co., NY, NY, "acetals", aldehydes, ketal, and ketone, pp. 5, 21, 322, 323.

Primary Examiner—Paul R. Michl
Assistant Examiner—Christopher D. RoDee
Attorney, Agent, or Firm—Foley & Lardner, Schwartz, Jeffery, Schwaab, Mack, Blumenthal & Evans

[57] ABSTRACT

A positive radiation-sensitive mixture is disclosed comprising a compound which forms an acid under the action of actinic radiation, and an acid-cleavable compound, the acid-cleavable compound producing, as cleavage product, an aromatically-substituted alcohol of the general formula I. The radiation-sensitive mixture according to the invention exhibits a wide processing latitude since different holding times do not cause any changes with respect to the development times. A high structural resolution is obtained with various developers 14 Claims, No Drawings

POSITIVE RADIATION-SENSITIVE MIXTURE AND RADIATION-SENSITIVE RECORDING MATERIAL PRODUCED THEREFROM

BACKGROUND OF THE INVENTION

The present invention relates to a positive radiation-sensitive mixture containing a compound which forms an acid under the action of actinic radiation, and an acid-cleavable compound.

Positive radiation-sensitive mixtures in which an acid is formed through the action of actinic radiation on a photoinitiator and the acid then, in a secondary reaction, renders the irradiated regions of an acid-cleavable material soluble in an appropriate developer have been known for some time.

Of the acid-cleavable components employed hitherto in this area, the following have proven successful:

(a) those containing at least one orthocarboxylic ester and/or carboxamide acetal group, it being possible for the compounds to have a polymeric character and it being possible for the groups mentioned to occur as linking elements in the main chain or as lateral substituents, (b) oligomeric or polymeric compounds containing recurring acetal and/or ketal groups in the main chain, (c) compounds containing at least one enol ether or N-acyliminocarbonate group, (d) compounds containing silyl ether groups, (e) compounds containing silylenol ether groups, and (f) cyclic acetals or ketals of β-keto esters or amides.

As components of radiation-sensitive mixtures, acid-cleavable compounds of type (a) are described in detail in EP-A-No. 0,022,571 and DE-A-No. 2,610,842; mixtures which contain compounds of type (b) are described in DE-C-No. 2,306,248 and DE-C-No. 2,718,254; compounds of type (c) are mentioned in EP-A-Nos. 0,006,626 and 0,006,627; compounds belonging to type (d) are presented in DE-A-No. 3,544,165 and DE-A-No. 3,601,264; compounds of type (e) can be found in U.S. application Ser. No. (corresponding to DE-A No. 3,730,783), filed simultaneously; compounds of type (f) are mentioned in EP-A-No. 0,202,196.

In DE-A-No. 2,610,842, compounds containing ortho -ester or -amide acetal groups in a radiation-sensitive copying material are described which are used in the production both of printing plates and microelectronic circuits. The alcohol components mentioned for such groups are alkyl, alkenyl and aryl radicals. Good results are reported for $C_1$ to $C_{18}$-aliphatic alcohols. Compounds based on the monoalkyl ethers of polyethylene glycols are also said to have comparable properties, the number of ethylene oxide units being, in particular, between 1 and 8. Investigations have now shown that good processing tolerances are always achieved when the alcohol component employed has a boiling point which is sufficiently high to prevent evaporation of the irradiated coating. When polyethylene glycol monoalkyl ethers are used, as when aliphatic alcohols are used, it is necessary to use relatively high-molecular-weight alcohol components. These in turn cause difficulties either with respect to the compatibility with the phenolic resins usually employed in coatings of this type or because of their effectiveness as plasticizers for the resin matrix. Finally, the etching resistance of coatings is reduced by long-chain aliphatic alcohols. Such coatings therefore survive certain process steps during production, for example of microelectronic components, with loss of resolution only.

The radiation-sensitive copying materials described in DE-A-No. 2,718,254 are also used for lithographic printing plates and for positive resists. They contain, as acid-cleavable component, an oligomeric compound containing recurring acetal or ketal units, whose alcohol component must be at least dihydric. In addition to the large range, due to the production process, within which the molecular weight or degrees of polymerization of such polyacetals may vary, the danger of introduction of contaminants into the radiation-sensitive mixture is particularly critical in the case of these acid-cleavable compounds since distillative purification is no longer possible. In addition, depending on the application conditions, the higher degree of polymerization means an increased danger of separation of the polymers employed in the case of the polymeric acetals and ketals mentioned here. This results in resolution losses, in particular when used in the submicron region.

In addition, it has recently been proposed, in contrast to the prior art, to use cyclic acetals or ketals of β-keto esters or amides as an acid-cleavable component which should also be suitable for use in photoresists (EP-A-No. 0,202,196). A disadvantage of these photoresists are their low radiation sensitivity.

SUMMARY OF THE INVENTION

It is therefore an object of the present invention to provide a positive radiation-sensitive mixture which exhibits no changes with respect to the development time during different "holding times" between irradiation and development, i.e., has a large processing latitude, meets the demands made on high structural resolution of the developed resist and retains this, even during the subsequent processing steps, and has uniformly good processability both in metal-ion-containing and metal-ion-free, aqueous-alkaline developers.

These and other objects are achieved by a positive radiation-sensitive mixture comprising a compound that forms an acid under the action of actinic radiation, and an acid-cleavable compound, which on acid-catalyzed hydrolysis yield a compound of general formula I

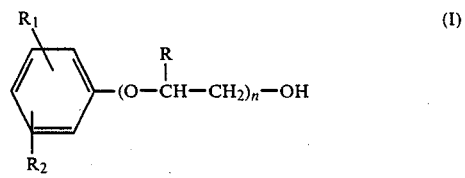

in which

R denotes hydrogen or alkyl, $R_1$ and $R_2$ may be identical or different and denote hydrogen, hydroxyl, halogen, cyano, nitro, alkyl, alkoxy, aryl or substituted carbonyl, in particular, arylcarbonyl- or alkylcarbonyl, or $R_1$ and $R_2$ together form a ring which is optionally substituted by $R_1$ and/or $R_2$, and n denotes 1 to 3, A positive radiation-sensitive recording material comprising a coating of the radiation-sensitive mixture on a substrate is also provided. A process for the production of an imaged radiation-sensitive recording material comprises the steps of applying a layer of the radiation-sensitive mixture to a substrate, drying the layer, irradiating the dried layer imagewise, and developing the layer in an aqueous-alkaline developer to produce an image.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

The acid-cleavable compounds according to the present invention produce cleavage products of the general formula I

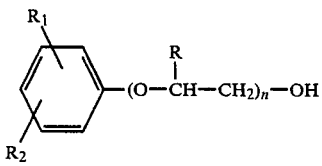

in which

R denotes hydrogen or alkyl, $R_1$ and $R_2$ may be identical or different and denote hydrogen, hydroxyl, halogen, cyano, nitro, alkyl, alkoxy, aryl or substituted carbonyl, in particular, arylcarbonyl- or alkylcarbonyl, or $R_1$ and $R_2$ together form a ring which is optionally substituted by $R_1$ and/or $R_2$, and n denotes 1 to 3.

It is particularly preferred when

R denotes hydrogen or methyl, $R_1$ and $R_2$ are identical and denote hydrogen or are different and one radical thereof is hydrogen, and the other is $(C_6-C_{10})$aryl, in particular, phenyl, optionally branched $(C_1-C_8)$alkyl, in particular, $(C_1-C_4)$alkyl, $(C_6-C_{10})$arylcarbonyl, in particular, phenylcarbonyl, $(C_1-C_8)$alkylcarbonyl, or halogen, in particular, bromine or chlorine, and n denotes 1 to 3.

If $R_1$ and $R_2$ are different and one radical thereof denotes hydrogen, the other radical is preferably in the para-position, where R denotes hydrogen or methyl, and n denotes 1.

If $R_1$ and $R_2$ are identical and denote, in particular hydrogen, then

R is preferably hydrogen or methyl, and n is 1 to 3.

Acetals or ketals whose alcohol component has a boiling point of greater than about 200° C. at 760 torr or is a solid at room temperature are particularly preferred.

Particularly favorable properties are achieved when the unsubstituted compounds of the general formula I are used with phenylglycol as the alcohol component, where n=1.

The acid-cleavable compounds used in the radiation-sensitive mixture according to the invention are acetals and ketals or orthocarboxylic esters and orthocarboxamide acetals. Preferred cleavable compounds are those that contain one or two acid-cleavable molecule groups, particularly preferably those that contain one acid-cleavable group per molecule. Efficient purification of the products, for example by distillative means, is insured in the case of these starting compounds.

Acetals and ketals are preferred, it having proven particularly favorable for the carbonyl compounds on which these acetals and ketals are based to have a boiling point above about 150° C. and a solubility in an aqueous-alkaline developer between about 0.1 and 100 g/l, as described in U.S. application Ser. No. (corresponding to German Patent Application No. P 3,730,785.1), filed simultaneously, in combination with the alcohol components disclosed here. (The contents of this application, and other references cited in the following description, are hereby incorporated by reference.) The content of acid-cleavable compound in the radiation-sensitive mixture according to the invention is about 2% to 30% by weight, preferably about 10% to 25% by weight, relative to the total weight of the coating.

Suitable components that, in the radiation-sensitive mixture according to the invention, preferably form or eliminate a strong acid on irradiation include a large number of compounds and mixtures thereof.

Diazonium, phosphonium, sulfonium and iodonium salts, halogen compounds, o-quinonediazide sulfochlorides and sulfonates and also organometallic/organohalogen combinations may be mentioned.

The diazonium, phosphonium, sulfonium and iodonium compounds mentioned are generally used in the form of their organic solvent-soluble salts, usually as deposition products with complex acids such as tetrafluoroboric acid, hexafluorophosphoric acid, hexafluoroantimonic acid and hexafluoroarsenic acid. Inter alia, these compounds are also mentioned in DE-A-No. 3,601,264.

The halogen compounds include, in particular, triazine derivatives, which are known from U.S. Pat. Nos. 3,515,552, 3,536,489 and 3,779,778, and DE-C-Nos. 2,718,259, 3,337,024, 3,333,450, 2,306,248, 2,243,621 and 1,298,414. However, they can also be used in combination with other photoinitiators, such as oxazoles, oxadiazoles or thiazoles, but also in mixtures with one another.

However, oxazoles, oxadiazoles, thiazoles or 2-pyrones which contain trichloromethyl or tribromomethyl groups are also known (DE-A-Nos. 3,021,599, 3,021,590, 2,851,472 and 2,949,396 and EP-A-Nos. 0,135,348 and 0,135,863).

Also included, in particular, are aromatic compounds which contain ring-bound halogen, preferably bromine. Such compounds are known from DE-A-No. 2,610,842 or are described in U.S. application Ser. No. (corresponding to German Patent Application No. P 3,730,784.3), filed simultaneously.

A representative of a combination with a thiazole which may be mentioned is one with 2-benzoylmethylene-naphtho-[1,2-d]thiazole (DE-A-No. 2,851,641 and DE-A-No. 2,934,758). A mixture of a trihalomethyl compound with N-phenylacridone is known from DE-A-No. 2,610,842.

Likewise, α-halocarboxamides (DE-A-No. 2,718,200) or tribromomethyl phenyl sulfones (DE-A-No. 3,503,113), that can be sensitized, for example, by benzophenone, benzil or Michler's ketone, are also suitable.

In general, the effectiveness of all the radiation-sensitive compounds described can be supported by photosensitizers. Anthracene, phenanthrene, pyrene, 1,2-benzanthrene, thiazines, pyrazolines, benzofurans, benzophenones, fluorenones, anthraquinones and coumarine derivatives, for example, may be mentioned. Their content is about 0.01% to 5% by weight, relative to the weight of the radiation-sensitive mixture.

Above all, triazine derivatives and aromatic compounds containing ring-bound halogen, in particular bromine, known from DE-A-No. 2,610,842 and U.S. application Ser. No. (corresponding to German Patent Application No. P 3,730,784.3), filed simultaneously, are particularly preferred.

Of the compounds mentioned in this copending application, those are preferred which have a $pK_a$ value of about 6 to 10, very particularly those which come under the general formula I

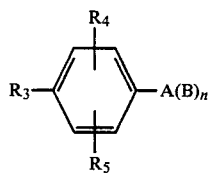 —A(B)$_n$ (I)

where

R$_3$ denotes carboxyl, OR' or SR',

R$_4$ and R$_5$ are identical or different and denote hydrogen, chlorine, bromine, alkyl, which is optionally substituted by aryl, alkoxy, aryloxy, hydroxyl groups or fluorine atoms; or aryl, which is optionally substituted by alkoxy, aryloxy or hydroxyl groups or by halogen atoms, R' denotes hydrogen, alkyl which is optionally substituted by aryl, alkoxy, aryloxy or hydroxyl groups or by fluorine atoms; aryl which is optionally substituted by alkoxy, aryloxy or hydroxyl groups or by halogen atoms; acyl, alkylsulfonyl, arylsulfonyl, alkoxycarbonyl, triorganosilyl, triorganostannyl or denotes an alkylene, arylene, bisacyl, sulfonyl, alkylenedisulfonyl, arylenedisulfonyl, diorganosilyl or diorganostannyl group whose second valency is bonded to the O atom of a further unit of the formula I, it being possible for the alkylene and arylene groups to be substituted in corresponding manner to the alkyl and aryl radicals, and n denotes 0 to 3.

whereby for n=0:

A denotes hydrogen, chlorine, bromine, alkyl, which is optionally substituted by alkoxy, aryloxy, hydroxyl or aryl radicals or by fluorine atoms; or aryl, which is optionally substituted by alkoxy, aryloxy, hydroxyl, carboxyl radicals or by halogen atoms, for n=1:

A denotes a single bond, —O—, —S—, —SO$_2$—, —NH—, —NR$_6$—, alkylene or perfluoroalkylene, for n=2:

A denotes —CR$_6$— or —N—, and for n=3:

A denotes —C—, and

B denotes

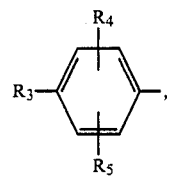

carboxyl, substituted carbonyl, in particular alkylcarbonyl or arylcarbonyl, carboxyalkyl or substituted sulfonylimidocarbonyl, and R$_6$ denotes alkyl, in particular, (C$_1$–C$_3$)alkyl, or aryl, in particular, phenyl.

These compounds are preferably only cleaved by high-energy radiation, i.e., short-wave radiation. In addition to UV radiation, this includes, above all, electron-beam radiation or X-ray radiation.

Besides monomeric radiation-sensitive acid formers, it is also possible to use polymers of this type. When monomeric initiators are used, their content is in the range of about 0.01% to 30% by weight, in particular, about 0.4% to 20% by weight, relative to the weight of the radiation-sensitive mixture.

If polymeric initiators are used, it may be possible to omit a polymeric binder. In addition, the polymeric initiator can be mixed with the binder; however, it is also possible for the monomeric components of a non-polymerized initiator to react with monomeric components of binders to form a co-condensate or copolymer. In this case, depending on the proportion of the polymer in this mixture, its content may also extend beyond the range described in the case of monomeric initiators. In particular, contents of greater than about 50% by weight and up to 100% by weight, relative to the weight of the radiation-sensitive mixture less the contents of the acid-cleavable compound, are included.

The radiation-sensitive mixture according to the invention may also contain a binder which is insoluble in water, and soluble, or at least swellable, in organic solvents and alkali. Such binders include, above all, phenolic resins of the novolak type. Phenol-formaldehyde resins, cresol-formaldehyde resins, the co-condensates and mixtures thereof are mentioned.

In addition, it is also possible to use vinyl polymers, such as poly(vinyl acetals), polymethacrylates, polyacrylates, poly(vinyl ethers), polyvinylpyrrolidones and styrene polymers, in each case optionally modified by comonomers, which are used alone or mixed with others.

The following may be mentioned in particular: polymers of styrene with alkenyl sulfonyl amino carbonyloxy or cycloalkenyl sulfonyl amino carbonyloxy units (EP-A-No. 0,184,804), polymers of acrylic acid, methacrylic acid, maleic acid, itaconic acid, etc., containing lateral, crosslinking —CH$_2$OR groups (EP-A-No. 0,184,044), polymers made of vinyl monomers and alkenylphenol units (EP-A-No. 0,153,682), polyvinylphenols as novolak substitute (DE-C-No. 2,322,230), polymeric binders containing lateral, phenolic hydroxyl groups (EP-A-Nos. 0,212,439 and 0,212,440), styrene-maleic anhydride copolymers (DE-A-No. 3,130,987), polymers made from unsaturated (thio)phosphinic acid iso(thio)cyanates with a polymer containing active hydrogen (DE-A-No. 3,615,612 and 3,615,613), polymers containing vinyl acetate, vinyl alcohol and vinyl acetal units (EP-A-No. 0,216,083), and poly(vinyl acetals)

containing units of hydroxyaldehydes (DE-A-No. 3,644,162).

The amount of binder is generally about 1% to 90%, in particular, about 5% to 90% by weight, preferably about 50% to 90% by weight, relative to the total weight of the radiation-sensitive mixture.

Furthermore, dyes, pigments, plasticizers, wetting agents and flow-control agents, but also polyglycols and cellulose ethers, for example, ethylcellulose, may optionally be added to the radiation-sensitive mixtures according to the invention in order to improve specific requirements, such as flexibility, adhesion and gloss.

The radiation-sensitive mixture according to the invention is preferably dissolved in solvents, such as ethylene glycol, glycol ethers, such as glycol monomethyl ether, glycol dimethyl ether, glycol monoethyl ether or propylene glycol monoalkyl ethers, in particular, propylene glycol methyl ether; aliphatic esters, such as ethyl acetate, hydroxyethyl acetate, alkoxyethyl acetate, γ-butyl acetate, propylene glycol monoalkyl ether acetate, in particular propylene glycol methyl ether acetate, or amyl acetate; ethers, such as dioxane, ketones, such as methyl ethyl ketone, methyl isobutyl ketone, cyclopentanone and cyclohexanone; dimethylformamide, dimethylacetamide, hexamethylphosphoric amide, N-methylpyrrolidone, butyrolactone, tetrahydrofuran, and in mixtures thereof. Glycol ethers, aliphatic esters and ketones are particularly preferred.

The solutions produced using the remaining components of the radiation-sensitive mixture generally have a solids content of about 5% to 60% by weight, preferably up to about 50% by weight.

A radiation-sensitive recording material is also provided according to the invention, essentially comprising a substrate and a radiation-sensitive mixture applied thereto.

Suitable substrates are all materials of which capacitors, semiconductors, multi-layered printed circuits or integrated circuits are comprised or from which they can be produced. In particular, surfaces which are made of thermally-oxidized and/or aluminum-coated silicon material and are optionally doped may be mentioned, including all other substrates that are customary in semiconductor technology, such as, for example, silicon nitride, gallium arsenide and indium phosphide. In addition, the substrates known for the manufacture of liquid-crystal displays, such as glass, indium/tin oxide; metal plates and foils, for example made of aluminum, copper or zinc; bimetallic and trimetallic foils; and also electrically nonconductive foils which are vapor-coated with metals, optionally aluminum-coated $SiO_2$ materials and paper, are suitable. These substrates may be subjected to thermal pretreatment and may be superficially roughened, etched or treated with chemicals in order to achieve desired properties, such as, for example, increased hydrophilicity.

In a particular embodiment, the radiation-sensitive mixture can contain an adhesion promoter for better adhesion, which may be contained in the resist formulation or applied between the resist and the substrate. In the case of silicon or silicon dioxide substrates, adhesion promoters of the aminosilane type, such as, for example, 3-aminopropyltriethoxysilane or hexamethyldisilazane, are suitable for this purpose.

Examples of substrates that can be used for the production of photomechanical recording layers, such as printing forms for letterpress printing, planographic printing, screen printing and rotogravure printing, and for the production of relief copies, include aluminum plates, optionally anodically oxidized, grained and/or silicated aluminum plates, zinc plates, steel plates, that have optionally been treated with chromium, and plastic films or paper.

The recording material according to the invention is irradiated imagewise. Suitable sources of actinic radiation include metal halide lamps, carbon arc lamps, xenon lamps and mercury vapor lamps. Irradiation with high-energy radiation such as laser, electron or X-ray radiation is preferred. Lasers which may be mentioned are, in particular, helium/neon lasers, argon lasers, krypton and xenon lasers, in particular krypton fluoride, xenon fluoride and helium/cadmium lasers.

The amounts of coating vary depending on the field of use. For example, when the radiation-sensitive mixture is applied to a printing plate, the preferred amount of coating is about 0.5 to 3.5 $g/m^2$. In general, the coating thicknesses are between about 0.1 and 100 $\mu m$, in particular, between about 1 and 10 $\mu m$.

The invention also provides a process for the production of a radiation-sensitive recording material. The radiation-sensitive mixture can be applied to the substrate by spraying, flow-coating, rolling, spin-coating and dip-coating. The solvent is then removed by evaporation, leaving the radiation-sensitive layer on the surface of the substrate. The removal of the solvents can be accelerated, if desired by heating the layer to temperatures of up to about 150° C. However, it is also possible to initially apply the mixture in the above-mentioned manner to an intermediate substrate from which it is transferred onto the final substrate material under pressure at elevated temperature.

The layer is subsequently irradiated imagewise. Actinic radiation is usually used, UV, X-ray or electron-beam radiation being particularly preferred. UV lamps which emit radiation of wavelength about 200 to 500 nm at an intensity of about 0.5 to 60 $mW/cm^2$ are usually used for irradiation. In the radiation-sensitive layer an image pattern is subsequently bared by development by treating the layer with a developer solution which dissolves or removes the irradiated regions of the material.

The developers used are solutions of alkaline reagents, such as, for example, silicates, metasilicates, hydroxides, hydrogen phosphates, dihydrogen phosphates, carbonates or hydrogen carbonates, in particular of alkali metal ions or ammonium ions, but also ammonia and organic ammonium bases and the like. The content of these substances in the developer solution is generally about 0.1% to 15% by weight, preferably about 0.5% to 5% by weight, relative to the weight of the developer solution. Developers which are free of metal ions are particularly preferred.

In order to increase the resistance to mechanical and chemical influences, in particular, to etching media, the developed coatings can be heated for some time, for example, about 5 to 40 minutes, at elevated temperature, for example, above 100° C., it being possible for the effect to be further supported by exposure with UV radiation.

The acetals present in the radiation-sensitive mixtures according to the invention can be prepared by condensation of the aldehyde or ketone with the alcohol with azeotropic distillative removal of the water of reaction. In another known variant, the aldehyde or ketone is reacted with trimethyl orthoformate to form the dimethyl acetal. In a second step, this is then reacted with an alcohol to form the desired acetal. Surprisingly, it has been found, in the preparation methods described below, that simultaneous addition of orthoester and alcohol to the carbonyl compound in the preparation of the acetals did not lead to transesterification products of the orthoester which are undesired here, but instead only the desired acetals were produced.

The preparation of the novel, acid-cleavable compounds present in the radiation-sensitive mixture according to the invention is illustrated by means of the examples below.

PREPARATION EXAMPLE 1

Benzaldehyde diphenoxyethyl acetal 0.5 g of p-toluenesulfonic acid was added with cooling to a mixture of 1 mol of benzaldehyde, 2 mol of phenoxyethanol and 1.1 mol of trimethyl orthoformate. The mixture was stirred for 2 hours at room temperature. A water-pump vacuum was subsequently applied to the mixing apparatus, and stirring was continued for 2 hours at each of 20° C., 40° C. and 60° C. The reaction mixture was subsequently passed through a thin-film evaporator at 80° C. and a pressure of 0.1 torr. Further distillation can take place, if desired, in the thin-film evaporator at appropriately elevated temperature.

The resultant acetal was stirred with $Na_2CO_3$, $K_2CO_3$ or basic aluminum oxide to neutralize the acid catalyst. The solid components were separated off and the filtrate was evaporated in vacuo. It was possible to employ the acetal in the present form in a recording material. It had a melting point of 22°–24° C.; no CO signal could be detected in the IR spectrum; the NMR spectrum ($CDCl_3$) exhibited an acetal signal at $\delta=5.76$ ppm.

The acetals and ketals of the following Preparation Examples were prepared analogously. Table I below contains a summary of the starting components (carbonyl and alcohol components) and the data for the resultant acetal or ketal (NMR signal and boiling or melting point):

TABLE I

| Preparation Examples | Carbonyl component | Alcohol component | NMR signal acetal: δ[ppm] | Boiling point °C./torr |
|---|---|---|---|---|
| H2 | piperonal | 4-tert-butyl-phenoxy-ethanol | 5.65 | |
| H3 | 2-ethyl-butanal | phenoxy-ethanol | 4.5 | 160/0.06 |
| H4 | benzaldehyde | 4-(2-hydroxy-ethoxy)-benzo-phenone | 5.49 | >170/0.1 |
| H5 | benzaldehyde | 4-bromo-phenoxy-ethanol | 5.76 | viscous oil |
| H6 | benzaldehyde | diethylene glycol monophenyl ether | 5.65 | viscous oil |
| H7 | benzaldehyde | triethylene glycol monophenyl ether | 5.60 | viscous oil |
| H8 | cyclo-hexanone | phenoxy-ethanol | | 129/0.01 melting point: 28° C. |
| H9 | orthoformic acid | phenoxy-ethanol | 5.49 | >200/0.05 |

For comparison, the acetals summarized in Table II, whose alcohol components do not come under those claimed in the invention, were prepared:

TABLE II

| Preparation Examples | Carbonyl component | Alcohol component | NMR signal acetal: δ[ppm] | Boiling point °C./torr |
|---|---|---|---|---|
| HV1 | cyclo-hexanone | polyglycol 200 | 1.25–1.75 3.45–3.75 | viscous oil |
| HV2 | benzaldehyde | n-hexanol | 5.50 | 128/0.1 |
| HV3 | cyclo-hexanone | methyl diglycol | 3.18 $CH_3O$ group | 140/0.01 |
| HV4 | orthoformic acid | n-butyl diglycol | 5.33 | |

In Table III, the boiling points (torr) of various alcohol components of general formula $R-(O-CH_2CH_2)_n-OH$ claimed in the mixture according to the invention are summarized. The alcohols where R=methyl or n-butyl, and hexanol are compared with these compounds as comparison examples.

TABLE III

| R | n = 1 °C./torr | n = 2 °C./torr | n = 3 °C./torr |
|---|---|---|---|
| methyl | 125/760 | 194/760 | |
| n-butyl | 171/760 | 231/760 | 278/760 |
| phenyl | 272/760 | 110/0.5 | 140/0.5 |
| 4-tert-butylphenol | 155/15 | | |
| benzophenone | m.p. 81° C. | | |
| hexanol | 156/760 | | |

The use examples which contain the radiation-sensitive mixture according to the invention, and also appropriate comparison examples are summarized below. The amounts are usually given in parts by weight (pw).

EXAMPLE 1

A coating solution was produced from 17 pw of a cresol-formaldehyde novolak having a softening range of 105°–120° C.,
5 pw of benzaldehyde diphenoxyethyl acetal (Preparation Example 1),
4 pw of tetrabromobisphenol A (Dow Chemical) in
74 pw of propylene glycol methyl ether acetate.

The solution was spin-coated at 3,000 rpm onto a silicon wafer which had been treated with an adhesion promoter (hexamethyldisilazane). After drying at 85° C. for 30 minutes in a circulation oven, a coating thickness of 1 μm was obtained. Imagewise irradiation was carried out using synchrotron radiation (BESSY, Berlin, air gap 2 mm) in a dose of 32 mJ/cm² through a gold-on-silicon mask. The experimental arrangement can be found in A. Heuberger, "X-Ray Lithography," *Microelectronic Engineering*, 3: 535–556 (1985). After a holding time of 5 minutes, the material was developed using an alkaline developer of the following composition:

5.3 pw of sodium metasilicate x 9 $H_2O$,
3.4 pw of trisodium phosphate x 12 $H_2O$,
0.3 pw of sodium dihydrogen phosphate, and
91 pw of demineralized water.

A flaw-free image containing all the details of the mask was obtained, even 0.3 μm lines and grooves having been reproduced without faults. The resist edges exhibited angles of virtually 90° (in a photomicrograph from a scanning electron microscope (SEM)).

EXAMPLES 2 TO 9

The procedure carried out was as in Example 1, with the difference that the acetal described there was replaced by the acetals from Preparation Examples H2 to H9 of Table I. The following results were achieved here in the developers from Example 1 and in a metal-ion-free developer (aqueous solution of tetramethylammonium hydroxide):

TABLE IV

| Example | Acetal | Development time in the developer from Example 1 | Development time in the metal-ion-free developer (0.3N) |
|---------|--------|--------------------------------------------------|-----------------------------------------------------|
| 2 | H2 | 120 s (0.3N) | 10 s (>60 s) |
| 3 | H3 | 60 s (0.3N) | 10 s ( 60 s) |
| 4 | H4 | 150 s (0.3N) | 20 s (>60 s) |
| 5 | H5 | 25 s (0.6N) | 20 s ( 60 s) |
| 6 | H6 | 90 s (0.3N) | 10 s ( 50 s) |
| 7 | H7 | 50 s (0.6N) | 25 s (>60 s) |
| 8 | H8 | 90 s (0.6N) | 10 s (>60 s) |
| 9 | H9 | 80 s (0.3N) | 10 s ( 40 s) |

All the acetals investigated had good developability in both types of developer and also a favorable developer resistance of the non-irradiated areas to the more aggressive metal-ion-free developer. The waiting time between irradiation and development did not affect the resolving power if it was at least 10 minutes and did not exceed 8 hours.

COMPARISON EXAMPLES V1 TO V4

The procedure was as in Example 1, but with the proviso that the acetal employed there was replaced by the acid-labile compounds from Table II. The results are summarized in Table V:

TABLE V

| Comparison Examples | Acid-labile compound | Development time in the developer from Example 1 (0.3N) | Development time in the metal ion-free developer (0.3N) | Remarks |
|---------------------|----------------------|---------------------------------------------------------|---------------------------------------------------------|---------|
| V1 | HV1 | 45 s | 6 s | Good tolerance in the waiting time between irradiation and development, but low developer resistance |
| V2 | HV2 | >120 s | 15 s | Low tolerance in the waiting time between irradiation and development |
| V3 | HV3 | >120 s | 15 s | Low resistance to the metal ion-free developer |
| V4 | HV4 | 60 s | 15 s | Low resistance to the metal ion-free developer |

In order to be able to estimate the thermal behavior of the radiation-sensitive mixture, the softening points of some mixtures according to the invention were compared with one another. The results obtained in this test are summarized in Table VI:

TABLE VI

| Mixture containing | Softening point (°C.) measured on the "Kofler bench" |
|--------------------|------------------------------------------------------|
| H5 | 123 |
| H6 | 120 |
| H9 | 106 |
| HV1 | 70 |
| HV2 | 110 |
| HV3 | 98 |
| HV4 | 100 |

As the present Examples and Comparison Examples show, it is only when the alcohol components employed according to the invention are used that it is possible to obtain a good development behavior in metal-ion-containing and metal-ion-free developers together with good thermal stability and plasma etching behavior. The use of other aldehyde components, corresponding to the prior art, in all cases leads to a poor property spectrum.

EXAMPLE 10

A coating solution was produced containing 5 pw of a poly(pyrocatechol monomethacrylate),
0.1 pw of 2-(4-ethoxynaphth-1-yl)-4,6-bis(trichloromethyl-s-triazine), and
1 pw of the acetal made from benzaldehyde and 4-bromophenoxyethanol (H5).

The coating solution was applied in a manner known onto a 0.3 mm thick aluminum printing plate substrate.

The aluminum substrate had previously been electrochemically roughened, anodized and rendered hydrophilic using poly(vinylphosphonic acid). After drying the coating, a coating weight of 1.6 g/m² was obtained.

The offset printing plate produced in this manner was covered with a copying mask and irradiated for 20 seconds with radiation from a high-pressure mercury lamp (5 kW) at a distance of 110 cm. The plate was developed using a developer from Example 1. A positive printing form of high resolution which gave 100,000 fault-free prints in an offset printing machine was obtained.

COMPARISON EXAMPLE V7

In this Comparison Example, the compound H5 was replaced by an acetal made from cyclohexanone and polyglycol 200 (HV1). Otherwise, the components corresponded to those from Example 10. However, it was only possible to produce less than 20,000 fault-free prints on an offset printing machine.

What is claimed is:

1. A positive radiation-sensitive mixture comprising:
a compound which forms an acid under the action of actinic radiation; and
an acid-cleavable acetal or ketal compound; wherein a compound of the formula I

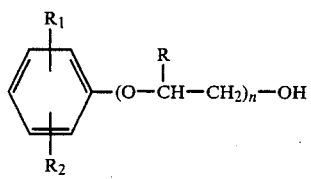

in which
R denotes hydrogen or alkyl,
$R_1$ and $R_2$ may be identical or different and denote hydrogen, hydroxyl, halogen, cyano, nitro, alkyl, alkoxy, aryl or substituted carbonyl, or
$R_1$ and $R_2$ together form a ring,
n denotes 1 to 3,
is formed as a cleavage product.

2. A radiation-sensitive mixture as claimed in claim 1, wherein the aldehyde or ketone component of the acid-cleavable compound has a boiling point above about 150° C. and a solubility in aqueous-alkaline developer of between about 0.1 and 100 g/l.

3. A radiation-sensitive mixture as claimed in claim 1, wherein the mixture additionally comprises a binder which is insoluble in water and soluble in aqueous-alkaline solution.

4. A positive radiation-sensitive recording material, comprising:
a substrate; and
a radiation-sensitive coating on said substrate comprising a radiation-sensitive mixture as claimed in claim 1.

5. A process for the production of an imaged radiation-sensitive recording material comprising the steps of:
applying a layer of a radiation-sensitive mixture as claimed in claim 1 to a substrate,
drying the layer;
irradiating the dried layer imagewise; and
developing the layer in an aqueous-alkaline developer to produce an image.

6. A process for the production of an imaged radiation-sensitive recording material as claimed in claim 5, wherein the substrate is irradiated imagewise in a microelectronic circuit pattern.

7. A radiation-sensitive mixture as claimed in claim 1, wherein $R_1$ and $R_2$ together form a ring that is substituted by at least one of $R_1$ and $R_2$.

8. A radiation-sensitive mixture as claimed in claim 1, wherein R denotes hydrogen or methyl and $R_1$ and $R_2$ are identical and denote hydrogen.

9. A radiation-sensitive mixture as claimed in claim 1, wherein R denotes hydrogen or methyl and one of $R_1$ and $R_2$ is hydrogen and the other is $(C_6-C_{10})$aryl, $(C_1-C_8)$alkyl, $(C_6-C_{10})$arylcarbonyl, $(C_1-C_8)$alkylcarbonyl, or halogen.

10. A radiation-sensitive mixture as claimed in claim 9, wherein one of $R_1$ and $R_2$ is phenyl, $(C_1-C_4)$alkyl, phenylcarbonyl, bromine or chlorine.

11. A radiation-sensitive mixture as claimed in claim 9, wherein $R_1$ is in a para-position with respect to $R_2$.

12. A positive radiation-sensitive recording material as claimed in claim 4, wherein the content of acid-cleavable compound in the radiation-sensitive mixture is about 2% to 30% by weight, relative to the total weight of the coating.

13. A radiation-sensitive mixture as claimed in claim 1, wherein the acid-cleavable compound comprises one acid-cleavable group per molecule.

14. A radiation sensitive mixture as claimed in claim 1, wherein $R_1$ and $R_2$ may be identical or different and denote arylcarbonyl or alkylcarbonyl.

* * * * *